United States Patent
Levine et al.

(10) Patent No.: US 7,300,460 B2
(45) Date of Patent: Nov. 27, 2007

(54) BIFURCATED GUIDEWIRE AND METHODS OF USE

(75) Inventors: Marc-Alan Levine, San Francisco, CA (US); Stephen Hebert, Berkeley, CA (US)

(73) Assignee: Counter Clockwise, Inc., San Francisco, CA (US)

( * ) Notice: Subject to any disclaimer, the term of this patent is extended or adjusted under 35 U.S.C. 154(b) by 877 days.

(21) Appl. No.: 10/335,034

(22) Filed: Dec. 31, 2002

(65) Prior Publication Data

US 2004/0127975 A1    Jul. 1, 2004

(51) Int. Cl.
*A61F 2/06*    (2006.01)
(52) U.S. Cl. ...................................... 623/1.35
(58) Field of Classification Search ............... 623/1.35, 623/1.1, 1.2, 1.51, 1.53, 1.22, 1.16; 606/191, 606/192, 194, 198
See application file for complete search history.

(56) References Cited

U.S. PATENT DOCUMENTS

| | | | |
|---|---|---|---|
| 4,994,071 A | 2/1991 | MacGregor | |
| 5,342,387 A | 8/1994 | Summers | |
| 5,669,924 A | 9/1997 | Shaknovich | |
| 5,749,825 A | 5/1998 | Fischell et al. | |
| 5,906,640 A | 5/1999 | Penn et al. | |
| 5,961,548 A | 10/1999 | Shmulewitz | |
| 6,056,775 A | 5/2000 | Borghi et al. | |
| 6,156,063 A | 12/2000 | Douglas | |
| 6,210,429 B1 | 4/2001 | Vardi et al. | |
| 6,264,682 B1 | 7/2001 | Wilson et al. | |
| 6,280,465 B1 | 8/2001 | Cryer | |
| 6,409,750 B1 | 6/2002 | Hyodoh et al. | |
| 6,514,281 B1 | 2/2003 | Blaeser et al. | |
| 6,520,988 B1 | 2/2003 | Colombo et al. | |
| 6,833,003 B2 | 12/2004 | Jones et al. | |
| 6,840,950 B2 | 1/2005 | Stanford et al. | |
| 6,890,349 B2 | 5/2005 | McGuckin, Jr. et al. | |
| 6,908,477 B2 | 6/2005 | McGuckin, Jr. et al. | |
| 6,939,368 B2 | 9/2005 | Simso | |
| 6,989,024 B2 | 1/2006 | Hebert et al. | |

FOREIGN PATENT DOCUMENTS

| | | |
|---|---|---|
| WO | WO 9639998 | 12/1996 |
| WO | WO 9745073 | 12/1997 |
| WO | WO 9934749 | 7/1999 |
| WO | WO 9936002 | 7/1999 |
| WO | WO 03041610 | 5/2003 |

*Primary Examiner*—Kevin T. Truong

(57) ABSTRACT

Described herein are methods and devices that may be useful, for instance, in thrombectomy and embolectomy procedures, stent delivery procedures, and procedures for bridging the neck of an aneurysm. The bifurcated guidewire device described herein comprises a proximal end, a distal end, a length therebetween, and at least one bifurcation branching the guidewire into at least two arms. The arms are controllable, which may be accomplished, e.g., by providing arms constructed of a shape memory material, or by providing mechanical methods to control the arms. The guidewire may have any number of bifurcations branching the guidewire into any number of arms as practicable. The arms may or may not have radio-opaque markers thereon or be constructed of a radio-opaque material. The arms may have webbing or a semi-permeable sac disposed between them to help capture natural or foreign matter therein. The guidewire may be used with or without a catheter.

15 Claims, 11 Drawing Sheets

BIFURCATED GUIDEWIRE AND METHODS OF USE

FIELD OF THE INVENTION

This invention relates generally to a bifurcated guidewire and its methods of use. More specifically, this invention relates to a bifurcated guidewire and methods for using it, for instance, to remove matter from within the vasculature, for delivering stents to bifurcated vessels, and for bridging the neck of an aneurysm.

BACKGROUND OF THE INVENTION

Procedures to treat vascular disease, such as angioplasty, atherectomy, and stenting, often create blood clots or dislodge material from the vessel walls. The clots (thrombi), and the dislodged material (emboli), enter the bloodstream and when large enough, occlude smaller downstream vessels blocking blood flow to tissue. Serious health risks, like stroke or even death, are created when the blockage occurs in the heart, lungs, or brain.

To combat these problems, several types of devices have been developed. Many of these devices employ the use of a filter, a basket type configuration, or a permeable sac to entrap the thrombi or emboli therein and these are often connected to the distal tip of a catheter or guidewire. Connecting these filters to a catheter or guidewire increases the overall profile of the device, which in turn diminishes its ability to negotiate through small vessels or tortuous anatomy. Consequently, it may be difficult or impossible to use these devices within vessels commonly found in the carotid artery and cerebral vasculature. Furthermore, many of these devices are incapable of preventing the material from escaping from the filter when the device is being removed from the body.

Many of these devices are also single functional. That is, their purpose is limited to the removal of emboli or thrombi from a patient's vasculature and they are incapable of being used for other purposes. One such purpose is the delivery of stents. Stent delivery to maintain passageways of blood vessels, biliary ducts, or other body lumens is well known. For example, stents are often deployed in an artery following a percutaneous transluminal coronary angioplasty (PTCA) procedure or a percutaneous transluminal angioplasty (PTA) procedure. The stent resists a tendency in the vessel to close, thus countering acute reclosure and plaque restenosis. A variety of stents and methods for delivering them are disclosed in the prior art. However, many of the typical prior art stents are incapable of being delivered and deployed within a bifurcated vessel.

One reason for this is that typically one branch of a bifurcated vessel is often larger in diameter than the other. Bifurcated stents and delivery systems have been developed in an attempt to overcome this problem. Many of them employ the use of multiple guidewires or multiple catheters, one for placement within each branch of the bifurcated vessel. However, entanglement of the wires often occurs because of the inability to control the movement of the wires. In addition, these devices often suffer from the same disadvantages above in that they often have large profiles, making them difficult to maneuver within small vessels and tortuous vasculature.

SUMMARY OF THE INVENTION

Described herein is a device that has a low profile and is controllable in accordance with each of its functions. The device may be particularly useful, for instance, in thrombectomy and embolectomy procedures, stent delivery procedures, and procedures for bridging the neck of an aneurysm.

One described device is a bifurcated guidewire device. The device comprises a proximal end, a distal end, a length therebetween and at least one bifurcation branching the guidewire into at least two arms. The arms are controllable, which may for example, be accomplished by providing arms constructed of a shape memory material. The arms may also be controlled using mechanical methods, such as a pullwire.

There may be any number of bifurcations for branching the guidewire into any number of arms as practicable. The arms may have radio-opaque markings or may have a portion constructed from a radio-opaque material. The arms may be of equal length or may be of different lengths, and some arms may comprise a RF element for delivering RF energy. The arms may also have webbing or a semi-permeable sac disposed between them, to help facilitate the capture of naturally occurring or foreign matter therein.

At least one of the guidewire arms may comprise a scooping member. The scooping member may further comprise webbing or a semi-permeable sac disposed between its members. The guidewire may further comprise a detachable joint, which may or may not be located at the site of the bifurcation. The detachable joint may be an electrolytic joint or it may be a sacrificial joint.

The device may further comprise a catheter, which may or may not have an optional port for the exit of at least one guidewire arm. The port may also be used to facilitate rapid exchange, and may be movable. An extension, having a port thereon may also be used to facilitate the exit of at least one guidewire arm. The extension may be adapted to fit onto the distal tip of the catheter.

The present invention also provides methods for delivering stents within bifurcated vessels. Described herein, e.g., are methods to deliver multiple stents to multiple branches of a bifurcated vessel. In some methods, portions of a bifurcated stent are delivered to different branches of a bifurcated vessel. In general, these methods involve the steps of providing a stent loaded bifurcated guidewire, advancing the guidewire within a bifurcated vessel and positioning it so that each stent loaded arm is within a different branch of the vessel, adjacent to a pre-selected treatment site. The stent or stents are then released and deployed, and the guidewire removed. A catheter may or may not be used. Similarly, radio-opaque techniques may be used to facilitate the delivery of the stents. The stents may or may not be radially self expanding.

The present invention also provides methods for capturing and removing natural or foreign matter from within an intraluminal space, for example, thrombi or emboli from within the vasculature. These methods generally comprise the steps of providing a bifurcated guidewire with controllable arms within an intraluminal space, positioning the guidewire next to the matter to be removed, manipulating the arms to capture the matter therein, and then removing the guidewire. A catheter may or may not be used.

The present invention also provides methods for bridging the neck of an aneurysm. These methods generally comprise the steps of providing a bifurcated guidewire having a detachable joint, advancing the guidewire to a pre-selected aneurysm site, positioning the guidewire arms along the inner walls of the aneurysm, detaching the arms at the detachable joint, and removing the guidewire. The detachable joint may be an electrolytic joint, a sacrificial joint, or some combination thereof. The joint may or not be located at the site of the bifurcation and radio-opaque techniques may or may not be used.

BRIEF DESCRIPTION OF THE DRAWINGS

The foregoing and other aspects of the present invention will best be appreciated with reference to the detailed description in conjunction with the accompanying drawings, wherein.

DETAILED DESCRIPTION OF THE INVENTION

Described herein are bifurcated guidewire devices that may be particularly useful, e.g., when performing angioplasty, stenting procedures, or atherectomy in critical vessels where the release of embolic debris into the bloodstream can occlude the flow of oxygenated blood to the brain or other vital organs. The bifurcated guidewire may also be suited for the removal of thrombi adhering to vessel walls, delivering stents within bifurcated vessels, and for bridging the neck of an aneurysm. While the profile of the guidewire may be made sufficiently small such that it is particularly useful in the cerebral vasculature, it may also be used in any intraluminal space where there is a need to remove naturally occurring or foreign matter.

Figure 1A:
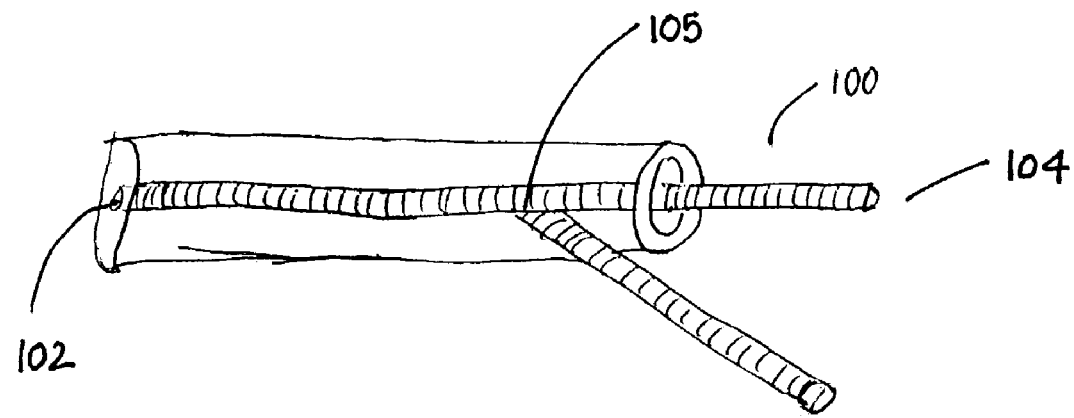
FIG. 1A illustrates how the bifurcated guidewire of the present invention may have one arm exiting a port on an optional catheter.
Figure 1A:
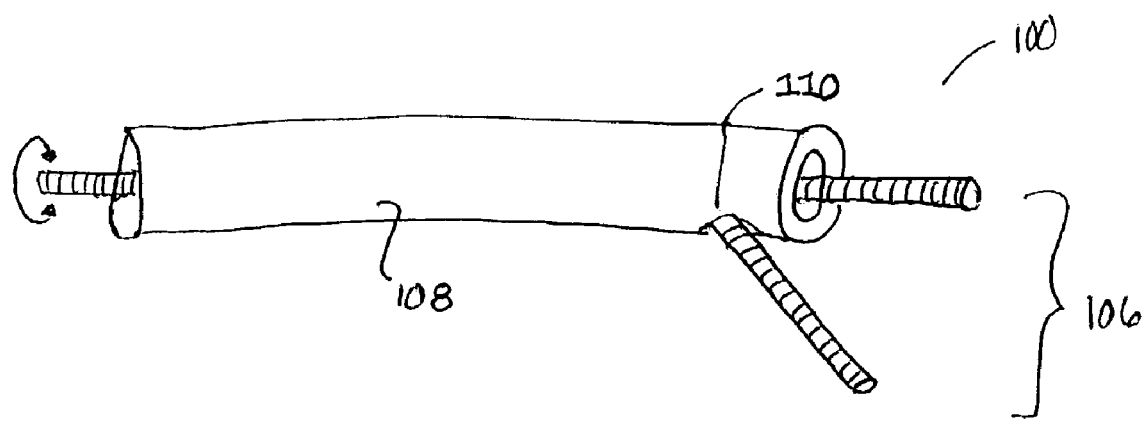

Turning now to the drawings, wherein like numerals indicate like elements throughout the views, there is shown in FIG. 1A a bifurcated guidewire 100 shown in one view with a surrounding catheter removed for clarity and another assembly view showing guidewire 100 positioned within a catheter. The guidewire comprises a proximal end 102, a distal end 104, and a length therebetween. The guidewire may be a conventional guidewire or may be formed from a hypotube. The guidewire may be of any length and be constructed of any suitable materials, e.g., superelastic metals such as Nitinol, platinum, or stainless steel. Typical lengths for a guidewire range from about 65 cm to about 320 cm and typical guidewire diameters range from about 0.008 inches to about 0.038 inches. The guidewire may be solid or may have a lumen therethrough, depending on the particular procedures in which it is to be used and the materials from which it is constructed.

Located in closer proximity to the distal end than the proximal end, is at least one bifurcation 105 that branches the guidewire into at least two arms 106. The guidewire may have any number of bifurcations, as practicable, branching the guidewire into any number of arms 106. In one variation, the guidewire has one bifurcation 105, branching the guidewire into two arms. As discussed in more detail below, one or both of the arms of the bifurcated guidewire may be controllable. In this way, they may help capture emboli therein and facilitate the delivery of stents.

FIG. 1A further illustrates how one arm of the guidewire may exit a port on an optional catheter 108. Any number of ports 110 may be used and the ports 110 may be of any size depending on the number of bifurcations and the diameter of each exiting guidewire arm. The port may be located at any position along the length of optional catheter 108. For example, the port may be located at a position in closer proximity to the distal end of the optional catheter or may be located at a position proximal thereto.

Figure 1B:
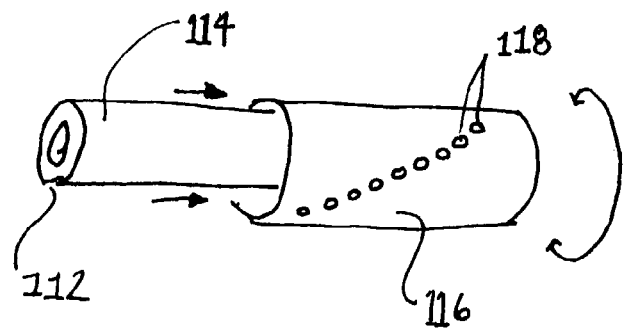
FIG. 1B illustrates how a port may be movable.
Figure 1B:
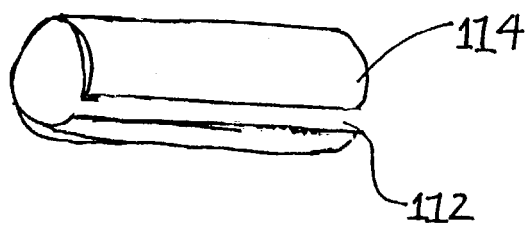

The port may also be movable along the length of the catheter. This may be accomplished, e.g., by providing a catheter that has an inner cylindrical member and an outer rotatable housing surrounding it, as shown in FIG. 1B. Slit 112 is longitudinally defined along at least a portion of the length of inner cylindrical member 114. Outer housing 116 has a plurality of openings 118 variously positioned along its length. As outer catheter housing 116 is rotated about its axis, one of a number of different openings 118 may correspondingly become aligned over slit 112. The catheter housing and inner member 114 may be of any lengths. The inner member and outer housing may comprise a single snap-fit unit to be attached to the distal tip of a catheter device. In this way, the port may be positioned at any desired location along the catheter length.

The port may also be positioned on the optional catheter using an extension having at least one port thereon. The extension may, e.g., comprise an additional length of catheter having a lumen therethrough and at least one port opening thereon. The extension may be made of any suitable material, e.g., the same material that the optional catheter is made of. The extension device may be connected to the distal tip of the catheter using any suitable method and be configured for use with any conventional catheter.

For example, the extension may be constructed of a low-temperature heat shrink material. The device may then be attached to the distal end of the catheter by heating the extension until it constricts, thereby tightly attaching itself to the catheter. The extension may also be attached to the distal tip of the catheter by a variety of snap-fit methods. The extension may also be attached to the catheter using a variety of locking mechanisms. A few such mechanisms are illustrated in FIGS. 1C and 1D.

Figure 1C:
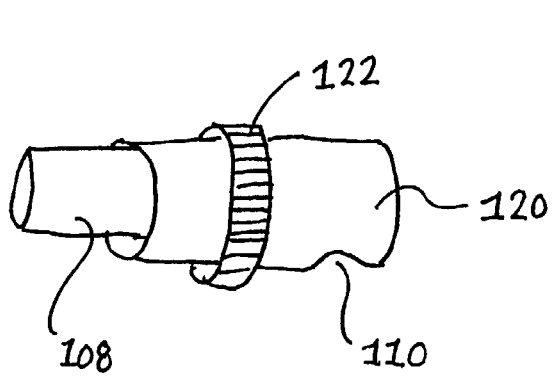
FIGS. 1C and 1D illustrate how an extension having a port thereon may be attached to a catheter.
Figure 1C:
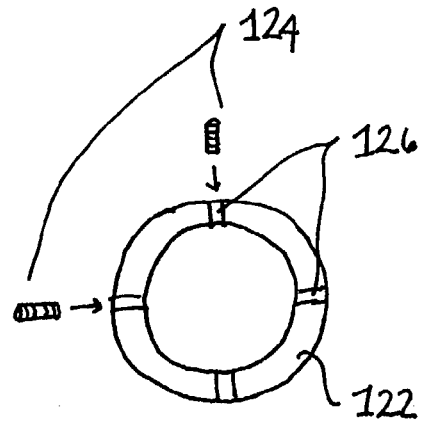
Figure 1D:
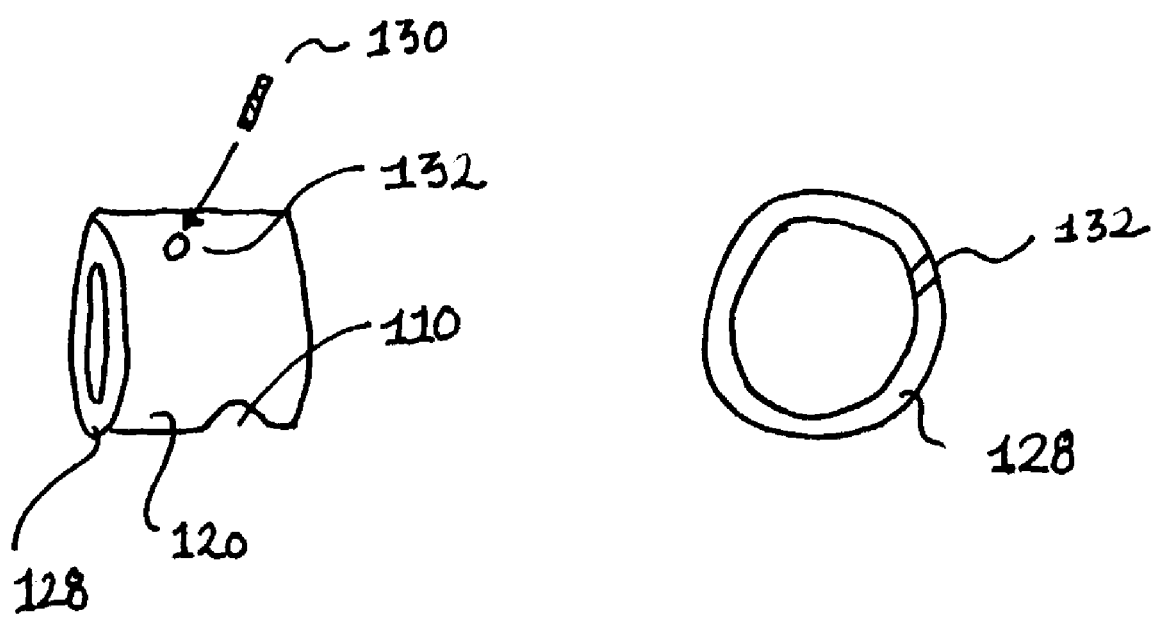

As shown in FIG. 1C, a locking collet 122 is used to secure the extension 120 to catheter 108. As shown therein, locking collet 122 surrounds a section of extension 120. Optional set screws 124 may be inserted into set screw holes 126 to tighten collet 122 onto the extension and secure the catheter therein. FIG. 1D shows how the extension may be attached to the catheter using an internal socket 128 with or without a set screw or locking mechanism. As illustrated therein, socket 128 fits within the lumen of the extension 120 and is configured to confine catheter 108 therein. A set screw 130 may be inserted into a set screw hole 132 located on extension 120. Set screw hole 132 is accessible from the outer surface of the extension and extends inwardly to contact catheter 108 such that when set screw 130 is inserted into set screw hole 132, socket 128 is tightened and catheter 108 secured therein. Any number of set screws and corresponding set screw holes may be used.

The extension may also be crimped onto the catheter using a hemostat or similar device. The extension may also be made of silicone or similar flexible material. In this way, the extension may simply be rolled on and off of the catheter. The extension may also be attached to the catheter using an adhesive, for example, Loctite glue. The lumen opening of the extension may be configured such that it aligns with, and corresponds to, the lumen of the optional catheter.

The port on the optional catheter may also be sufficient in size to facilitate rapid exchange of devices therethrough. In this way, guidewire 100 need not exit at the proximal end of optional catheter 108. In turn, this may reduce the necessary guidewire exchange length and facilitate quicker exchange of devices thereby. Alternatively, the rapid exchange port need not be the same port used for exit of a guidewire arm. Additional ports may optionally be provided at desirable locations along the length of the optional catheter to facilitate rapid exchange of devices therethrough. In this way, devices can more quickly and conveniently be withdrawn while maintaining the guidewire in place, since the exchange portion manipulated by a physician is close to the point of entry into the patient.

Figure 1E:
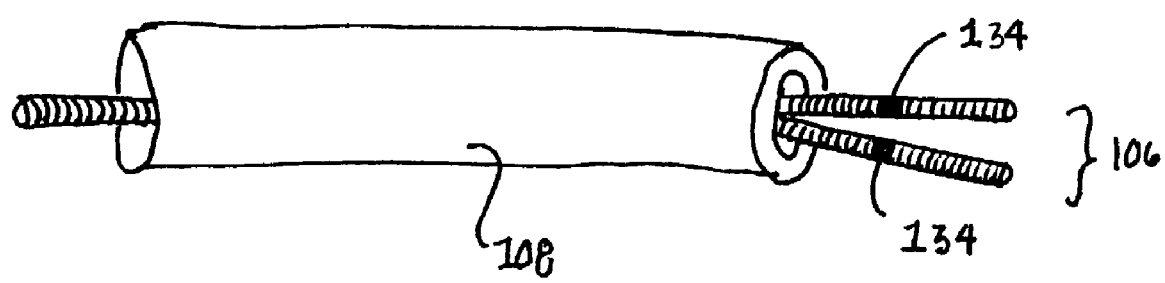
FIG. 1E illustrates how the bifurcated guidewire of the present invention may have arms that exit the lumen of an optional catheter at its distal end.

Arms 106 need not exit a port on an optional catheter. For example, arms 106 may exit the lumen of optional catheter 108 at its distal end, as illustrated in FIG. 1E. While illustrated in FIG. 1E without a port located thereon, the optional catheter may still comprise one or several ports if desirable. For example, in the case of a multiple bifurcated guidewire, some arms may exit the lumen of the catheter, while other arms may exit ports located along the length of the catheter body.

As mentioned above, arms 106 may be controllable. In this way, they may have the capacity to engage and retain any naturally occurring or foreign matter for removal from within an intraluminal space. In this regard, any number of suitable materials may be used to construct arms 106 and the arms may be controllable in any number of ways. The guidewire arms may or may not be constructed from the same material as the guidewire body itself.

For example, the arms may be constructed of a shape memory material such as, nickel-titanium alloys (e.g., Nitinol), nickel-titanium-cobalt alloys, other transition and precious metal alloys or thermoplastic heat settable materials that exhibit shape memory characteristics. Shape memory materials are well known in the art as having the ability to assume different shapes upon the application of shape memory effecting behavior. Shape memory behavior may be effected, for example, by the application of heat or by the induction of stress. Constructing the guidewire arms from a shape memory material allows the guidewire to have a first, reduced profile shape so it can traverse easily through a catheter and tortuous anatomy, and a second expanded shape, so it can capture thrombi or emboli within its arms.

Arms 106 may comprise Nitinol and shape memory behavior may be effected by raising the temperature of guidewire 100. This may be accomplished, for example, by induction heating, immersion heating, application of RF energy, or by any similar mechanism capable of heating the arms. Guidewire 100 may comprise a heating element that facilitates the shape memory effect necessary to plastically deform the arms. If the guidewire body is also constructed of a shape memory material, the materials that have been selected are typically such that each is within a desirable range of plastic deformation.

Figure 1F:
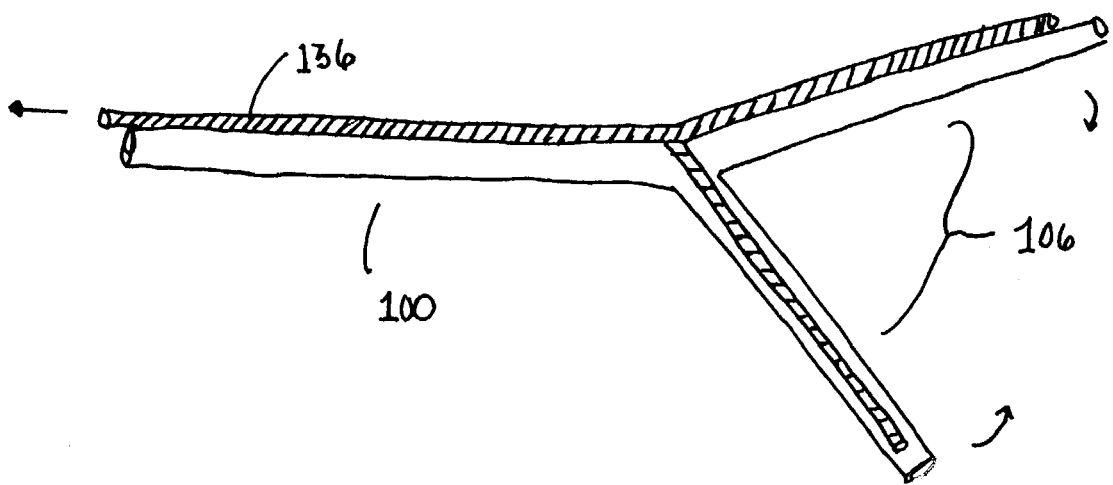
FIGS. 1F and 1G illustrate how a pullwire may be used to control the arms of the guidewire.
Figure 1G:
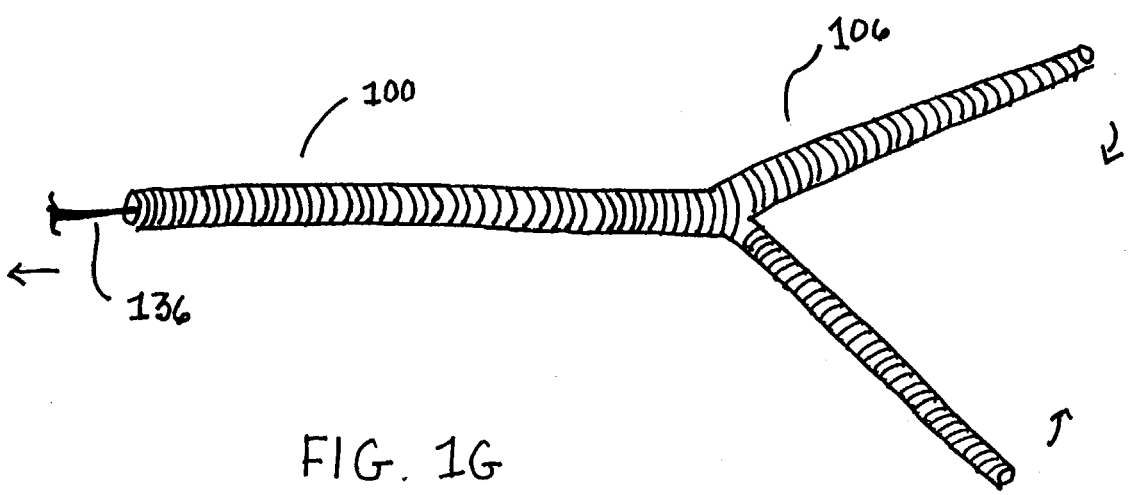

Arms 106 may also be controlled using mechanical methods, using e.g., any mechanism capable of effecting a selectively desired response. For example, a pullwire configuration may be used as illustrated in FIGS. 1F and 1G. The pullwire may be a portion of the guidewire itself and be configured such that when pulled proximally, a downward force is exerted on arms 106, causing them to close. Similarly, the pullwire may not be a portion of the guidewire, but instead be a separate wire. FIG. 1F illustrates how pullwire 136 may be positioned along a surface of guidewire 100 for controlling arms 106. FIG. 1G illustrates how the pullwire may be placed within the lumen of the guidewire. The pullwire described herein need not traverse the entire length of the guidewire and its corresponding arms. The pullwire may be made of any length sufficient to control arms 106. For example, the pullwire may be a push-pull wire such that when the wire is pulled proximally, a downward force is exerted on arms 106 causing them to close. In this example, when the push-pull wire is pushed distally a force is exerted on the arms causing them to open. Similarly, the pullwire may be configured to be biased outwardly, such that pulling the pullwire proximally causes arms 106 to close and releasing the pullwire, causes arms 106 to open. The methods hereinabove described for controlling arms 106 are merely illustrative and it should be understood that any number of suitable mechanisms may be used. Such use of alternative mechanisms is expressly contemplated by the present invention.

In addition, radio-opaque markings may be placed on guidewire arms 106 at any position along their length, or a portion of the arms themselves may be constructed of a radio-opaque material. For example, FIG. 1E shows each arm 106 having a radio-opaque marking 134 located at a position close to the center of its length. Similarly, a portion of the optional catheter or guidewire body may comprise a radio-opaque material. Radio-opaque materials, e.g., gold, silver, platinum, etc., are well known in the art for helping to indicate location and facilitate object positioning. Thus, the use of radio-opaque techniques with the present invention may be helpful in carrying out the methods described herein above and below. Alternatively, radio-opaque material may not be used at all with arms 106.

Figure 1H:
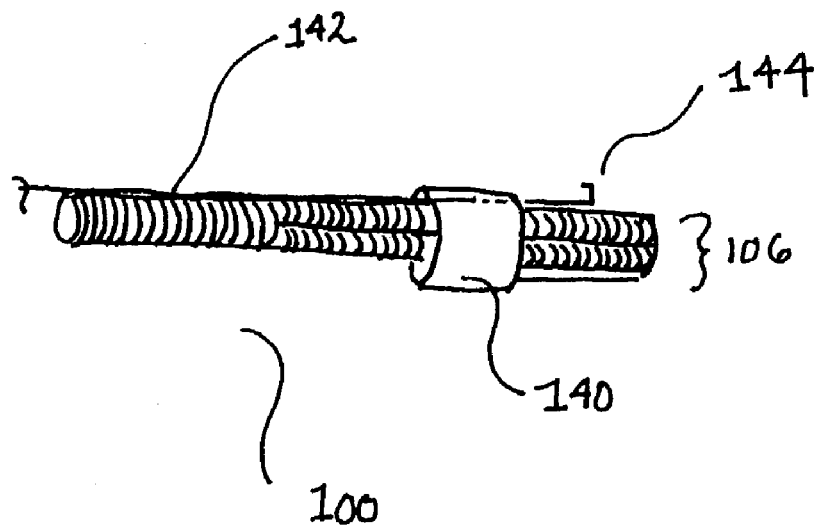
FIG. 1H illustrates how a sheath may be employed to surround the guidewire arms.

Arms 106 may be of equal length or may be of different lengths. In some variations it is desirable that the arms be of different lengths. For example, having one arm longer than the others may help facilitate stent delivery within a branched vessel having branches of varying lengths. Having arms of different lengths may also be useful in facilitating the capture of thrombic or embolic material. A sheath may optionally be employed for surrounding the guidewire arms, thereby facilitating the low profile nature of the guidewire arms, as illustrated in FIG. 1H. As shown in FIG. 1H, sheath 140 surrounds arms 106 of guidewire 100. The sheath may then be retracted at a desirable time. For example, a pullwire 142 having a hook 144 at its distal end may be used to facilitate sheath removal. The guidewire arms may also comprise a RF element. The RF element may be located at the distal tip of the arms or at any other desirable location. In this way, the arms may be positioned adjacent to an area where it is desirable to deliver RF energy, and the RF element employed to deliver it.

Figure 1I:
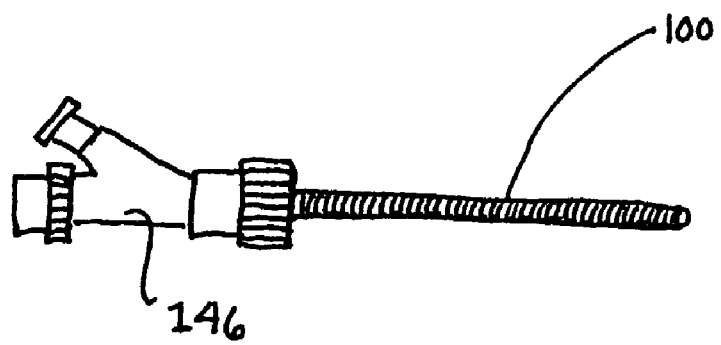
FIG. 1I illustrates how a luer lok, Touhy Borst adapter, or other port may be used in connection with the device of the present invention.

A luer lok, Touhy Borst adapter, or other similar port may be used in connection with the present invention. For example, as shown in FIG. 1I, a luer lok 146 may be attached directly to the proximal end of the bifurcated guidewire 100. Alternatively, a luer lok may instead be attached to the proximal end of an optional catheter. In FIG. 1I, guidewire 100 is one having a lumen so that any desirable fluid may be introduced through the port and pass therethrough. Luer loks and such similar ports are well known in the art and it is contemplated that any suitable port may be used with the present invention. Similarly, it is contemplated that the port be attached in any suitable fashion. For example, the port may be attached by compression, by heat shrinking, by welding, by brazing, by soldering, or any of the methods described above with respect to the extension. When a lok or port is used in combination with the present invention, any number of desirable fluids may be introduced. In some instances, it may be desirable to introduce a pressurized saline solution, for e.g., during the delivery or deployment of a stent. In other instances, it may be desirable to introduce other fluids.

The optional catheter may have any number of configurations. It may be of any desirable length and be made of any suitable material. Conventional catheters standard in the industry may be used with the guidewire of the present invention, or a specially manufactured catheter may be used instead. Catheters of various types are well known in the art, and it is contemplated that any suitable catheter may be used. As mentioned above, the optional port for exit of the guidewire arms may be located on an extension that is attached to the distal tip of the optional catheter. When an extension is used, it is desirably made to fit onto the distal tip of the catheter to be used.

Figure 1J:
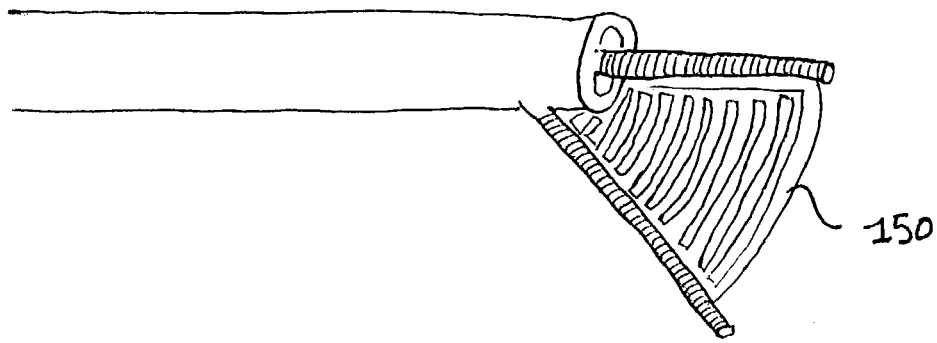
FIGS. 1J-1L illustrates how webbing or a semi-permeable sac may be disposed between the arms of the bifurcated guidewire.
Figure 1K:
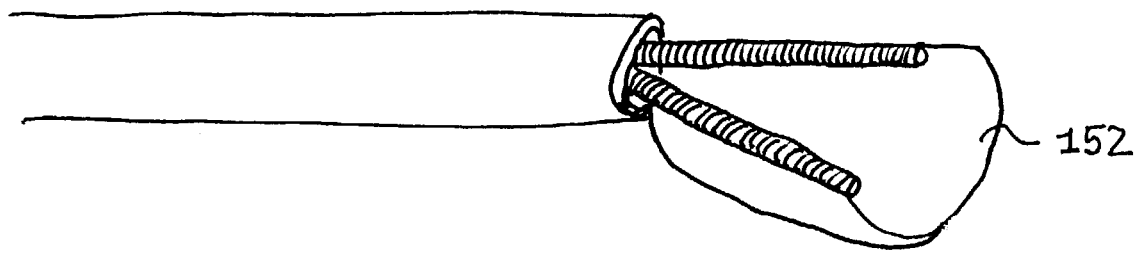

The arms of the bifurcated guidewire may have webbing or a semi-permeable sac disposed between them as shown in FIGS. 1J and 1K respectively. The webbing or sac may be made of any suitable material. Such materials are those allowing blood cells to pass through substantially unhindered, while prohibiting emboli or thrombi from doing so. For example, the webbing 150 or semi-permeable sac 152 may be made of a thin, flexible, biocompatible and semi-permeable material. The webbing for example, may be made of a thermoplastic elastomer, for example, a block copolymer of styrene-ethylene-butylene-styrene, such as C-FLEX. The webbing may also be constructed of collagen, polyethylene, polypropylene, polyurethane, polyester, polyethylene tetraphlalate, nylon polytetrafluoroethylene, or any combinations thereof.

The webbing may be used with the guidewire in any desirable configuration. For example, the webbing may be attached to the arms of the guidewire when one of the guidewire arms exits a port on the optional catheter. Similarly, the webbing may be attached to the arms of the guidewire when all of the guidewire arms exit the lumen of the optional catheter. Alternatively, the webbing may be attached to the guidewire arms when the optional catheter is not employed.

Figure 1L:
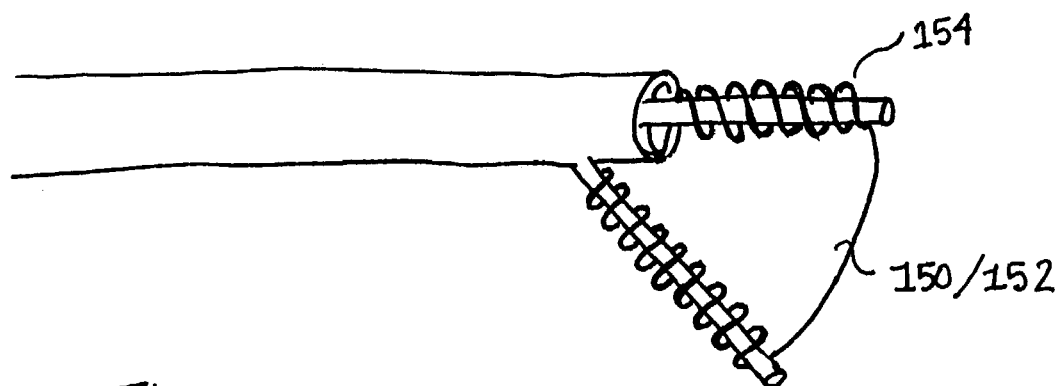

The webbing may be attached to the guidewire arms using any suitable methods. For example, the webbing may be attached to the arms using a biocompatible adhesive or glue. Similarly, a portion of the webbing may be wrapped around a portion of each guidewire arm. For example, the webbing may be woven or threaded onto each guidewire arm as shown in FIG. 1L by 154. Any suitable materials may be used to thread the webbing in this fashion, for example a flexible and durable polymer may be used, or a thin strand of flexible metal may be used instead.

Figure 2A:
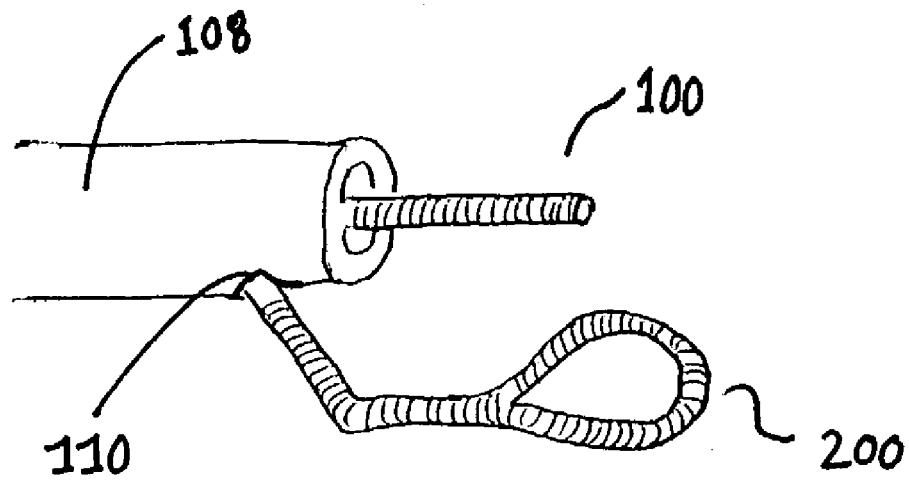
FIGS. 2A and 2B illustrate how at least one arm of the bifurcated guidewire of the present invention may comprise a scooping member for capturing thrombi or emboli.
Figure 2B:
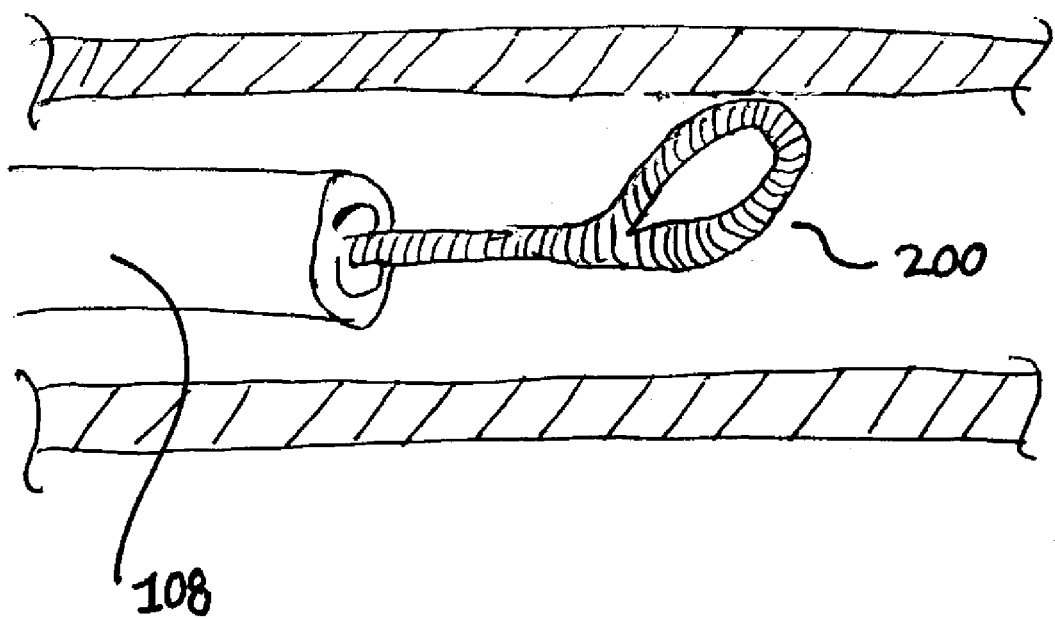

FIGS. 2A and 2B illustrate how at least one arm of the bifurcated guidewire may comprise an optional scooping member for capturing thrombi or emboli therein. The scooping member 200 may take on any number of configurations. For example, the scoop may exit port 110 on optional catheter 108 as shown in FIG. 2A, or scoop 200 may exit the lumen of optional catheter 108 as shown in FIG. 2B. Similarly, the scoop configuration may be used without a catheter (not shown).

The scoop may have any cross-sectional configuration and be formed from any number of materials. Such materials include those rendering the scoop controllable in order to facilitate the capture of thrombi or emboli therein. For example, any of the shape-memory materials described in detail above may be used. The scoop may, e.g., be formed of Nitinol. The shape memory behavior may be effected by the application of heat or by the induction of stress, as described above. The guidewire may e.g., comprise a heating element for effecting shape-memory behavior.

During release and retrieval, the scoop has a first, low profile shape. In this first shape, it is collapsed so that, if desirable, it may fit within a catheter. The guidewire may then be advanced distally within an intraluminal space, so that the scoop is located at a position adjacent to a pre-selected treatment site. In this respect, optional radio-opaque markings may be placed at any position along the scoop, or a portion of the scoop itself may be constructed of a radio-opaque material. Once the scoop has been advanced to its desired position, shape memory behavior is effected. In response, the scoop expands to a second shape, so that emboli or thrombi may be caught therein. In this way, the scoop can provide a high degree of efficacy in capturing emboli or thrombi, while maintaining a low profile when not in use.

The scoop need not be formed of a shape memory material, and may be instead controlled using mechanical methods. For example, the scoop may be connected to an elongate pullwire, which may or may not be a portion of the guidewire body itself. The pullwire in this configuration may be operated in a similar fashion as that described above and illustrated in the corresponding figures. For example, as the pullwire is pulled proximally, a downward force may be exerted on the arms of the scoop member, causing them to collapse together. In a similar manner, as the pullwire is pushed distally, the arms may expand outwardly causing the scoop to assume its second, expanded shape. Of course, this configuration may be reversed so that as the pullwire is pulled proximally, the arms expand and that as it is pushed distally, the arms collapse.

In operation, the scoop may be maneuvered to engage a thrombus or embolus therein. This may be accomplished, for example, by moving the scoop distally past and below the matter to be captured and the moving it upward, capturing the matter therein. In this respect, the webbing material or semi-permeable sac described in detail above may be disposed between the arms of the scoop to help facilitate the capture of material. The webbing or sac may be attached to the scoop arms in a manner substantially similar to that described above. The vessel wall may also be used to further aid in the capture of the material by providing a support for the scoop to gently compress against. After the scoop has entrapped the desired matter therein, the scoop arms are then collapsed and the guidewire pulled proximally. If a catheter is used, it is then withdrawn with the guidewire and the trapped material therein. However, the scoop may also be operated without the optional catheter.

Figure 3A:
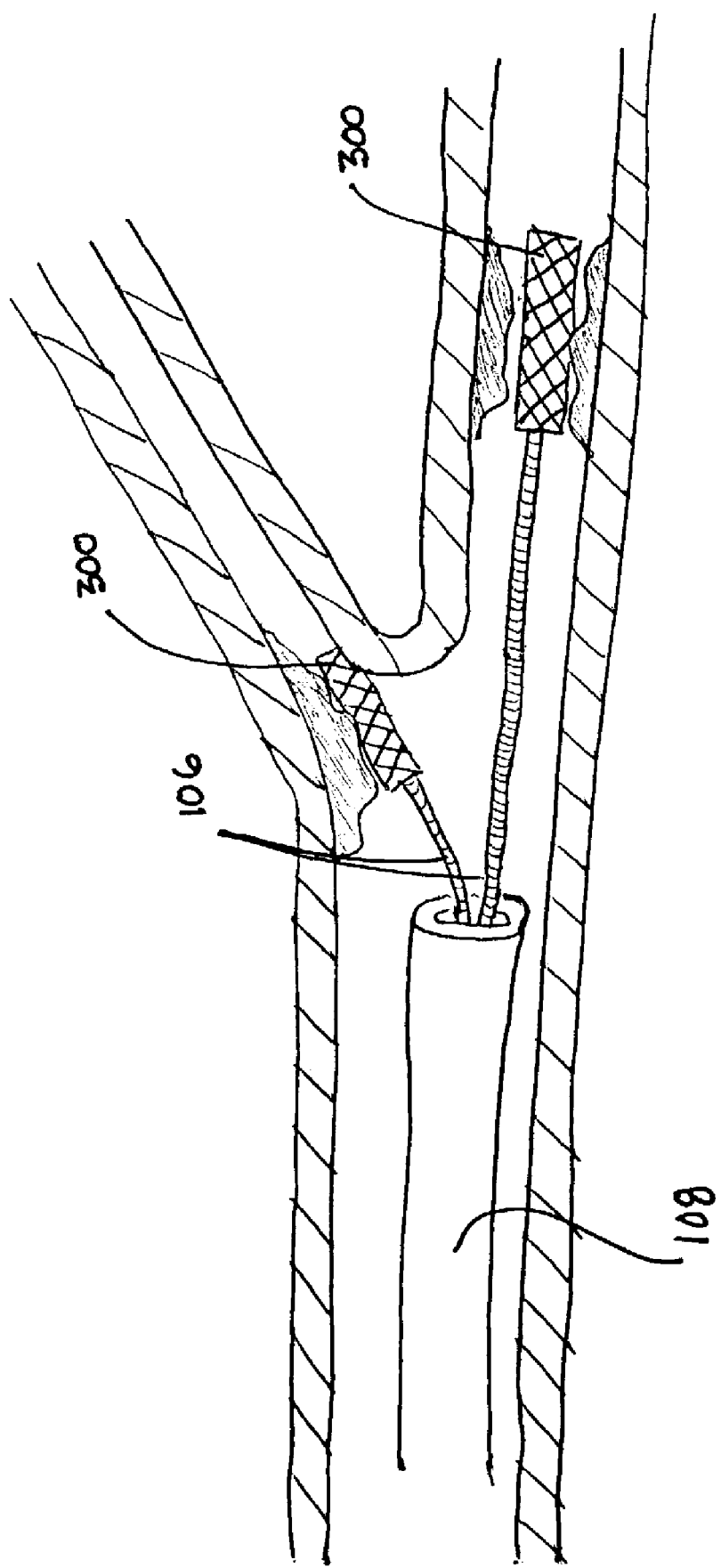
FIGS. 3A and 3B illustrate how the present invention may be used to deliver stents within bifurcated vessels.
Figure 3D:
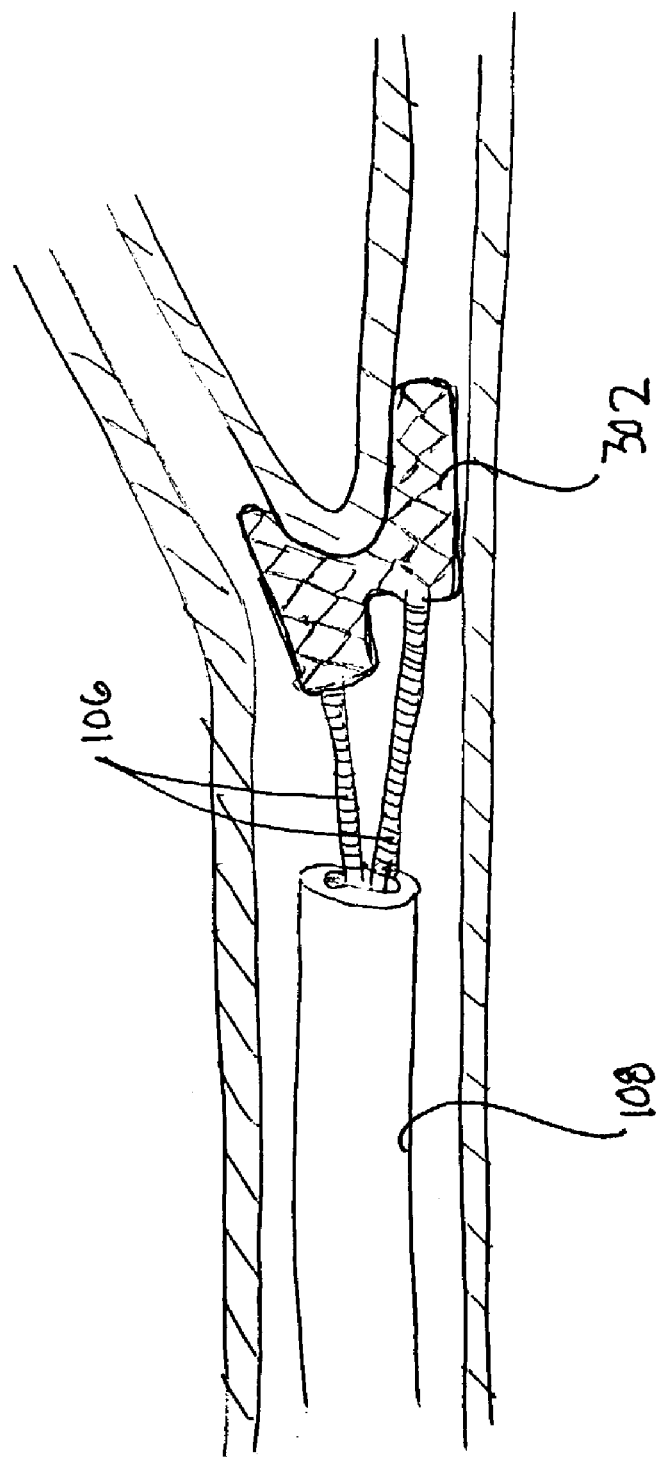

The present invention also provides methods for delivering stents within bifurcated vessels as shown in FIGS. 3A and 3B. Any type of stent may be used in combination with the present invention depending upon the procedure to be performed. For example, radially self-expanding stents (with or without an outer sheath) may be used, or balloon expandable stents may be used instead. FIG. 3A illustrates how the bifurcated guidewire of the present invention may have stent loaded arms for introduction into two branches of a bifurcated vessel. As shown therein, each arm 106 of the bifurcated guidewire may have a stent 300 loaded thereon. The loading of stents onto a guidewire is described in detail in Applicant's co-pending application, U.S. Ser. No. 10/087,127 entitled, "Guidewire Loaded Stent for Delivery Through a Catheter" filed for on Feb. 28, 2002, which is hereby incorporated by reference in its entirety. FIG. 3B illustrates how the present invention may be used to deliver a bifurcated stent. In this variation, a bifurcated stent 302 is loaded onto the arms 106 of the bifurcated guidewire.

As depicted in FIGS. 3A and 3B the bifurcated guidewire arms are loaded with radially self-expanding stents. The guidewire may first be advanced distally to a pre-selected treatment location. The stents may then be released therefrom. This may be accomplished in any number of ways. For example, this may be accomplished using a pressurized saline solution that is introduced through a port located at the proximal tip of the catheter or guidewire, as described above. Once the stent has been released, it is left to radially self expand. However, there are a variety of different stent delivery and deployment techniques known in the art and it is expressly contemplated that all suitable techniques of stent delivery and deployment may be used with the present invention. For example, in configurations in which the guidewire has a lumen, an expandable balloon may be placed at a position along the guidewire surface, for use in expanding a stent.

The present invention also provides methods for using the bifurcated guidewire device with an aneurysm. For example, the guidewire may have detachable arms, which may be useful, in bridging the neck of an aneurysm. Similarly, detachable arms may be useful in stabilizing the placement of vaso-occlusive devices, such as helically wound coils, within an aneurysm. FIGS. 4A-4E illustrate how the arms of the bifurcated guidewire are detachable and used to stabilize the placement of vaso-occlusive coils. While FIGS. 4A-4E show a guidewire having two arms, any number of arms may be provided. For example, in some situations it may be desirable to have a greater number of detachable arms to ensure the vaso-occlusive devices are adequately trapped within the aneurysm.

Figure 4A:
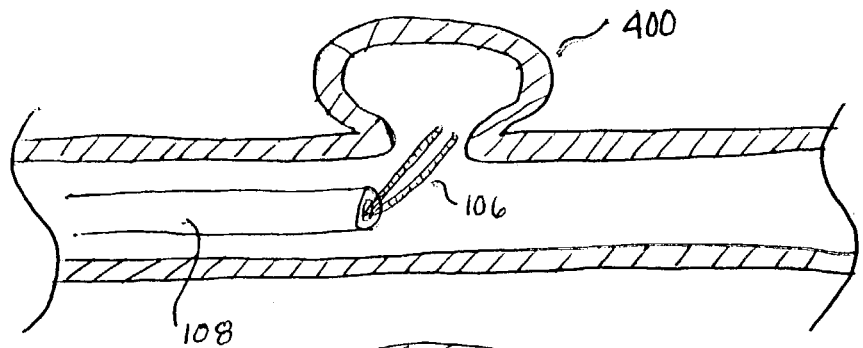
FIGS. 4A-4E illustrate how the present invention may be used to bridge the neck of an aneurysm.

Beginning first with FIG. 4A, there is shown therein, how optional catheter 108 may be advanced distally to the site of aneurysm 400 emanating from an artery wall. The bifurcated guidewire may be disposed within the optional catheter lumen and extend distally past it. As described above, the catheter may have radio-opaque markers located on a portion of its length, or similarly, arms 106 may utilized radio-opaque technology. In this way, placement of the catheter and the guidewire arms at the site of the aneurysm may be facilitated.

Figure 4B:
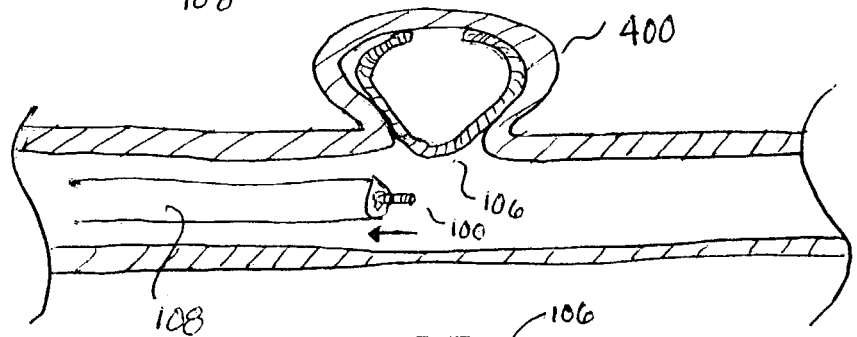

FIG. 4B shows how guidewire arms 106 are detached once they have been appropriately placed along the inner walls of the aneurysm. Any number of methods may be used to detach arms 106 from the guidewire body. For example, an electrolytic joint may be used and the joint may be dissolved by the application of heat. Similarly, a sacrificial joint may be used to facilitate the detachment of arms 106.

The sacrificial joint may comprise a portion of the guidewire susceptible to dissolution via electrolysis in blood or other ionic media. In this way, the sacrificial joint portion will dissolve, while the remaining portions of the guidewire will not. In order to ensure that only the joint portion will dissolve, the guidewire arms should be constructed of a suitable material, or instead, be suitably coated. Examples of suitable material include insulating materials like polyfluorocarbons, polyurethane, polyethylene, polypropylene, polyimides, and other polymeric materials. The sacrificial joint typically is not coated with these materials, but is instead constructed of a non-insulated material, for example, stainless steel. In this way, only the joint portion is dissolved in the blood. Exemplary joints that may be used in combination with the present invention are provided in U.S. Pat. No. 5,122,136 to Guglielmi et al, U.S. Pat. No. 5,354,295 to Guglielmi et al., U.S. Pat. No. 5,624,449 to Pham et al., all of which are hereby incorporated by reference in their entirety.

In FIG. 4B, the joint has been dissolved leaving the arms to bridge the neck of the aneurysm. The arms are sufficiently recessed within the aneurysm and do not protrude significantly into the artery. In this way, blood or fluid flow is not blocked therethrough. After the arms are detached, the remaining guidewire may then be withdrawn from the catheter, or the entire catheter device may be withdrawn instead.

Figure 4C:
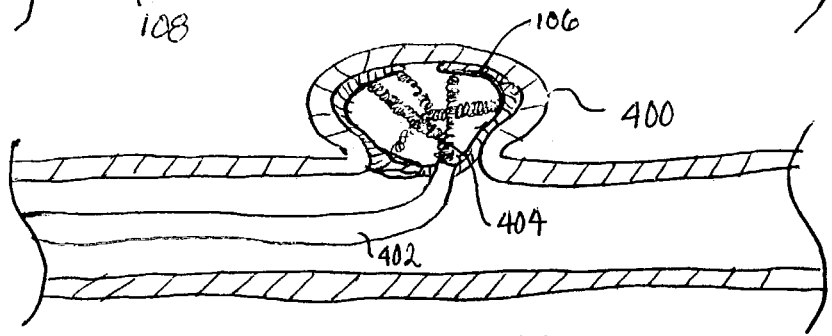
Figure 4D:
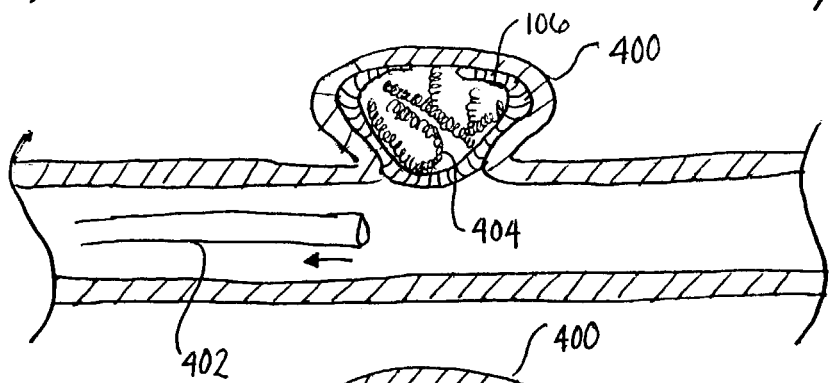

Moving next to FIG. 4C, there is shown therein the introduction of a delivery catheter for delivery of the vaso-occlusive coils to the aneurysm. Delivery catheter 402 may be the same as optional catheter 108 if suitably sized, or it may be a different catheter, introduced into the artery for the purpose of delivering the vaso-occlusive coils. As shown in FIG. 4C, an alternate delivery catheter 402 is used to deliver vaso-occlusive coils 404. Once vaso-occlusive coils 404 are delivered within the aneurysm, delivery catheter 402 may be withdrawn, as shown in FIG. 4D.

Figure 4E:
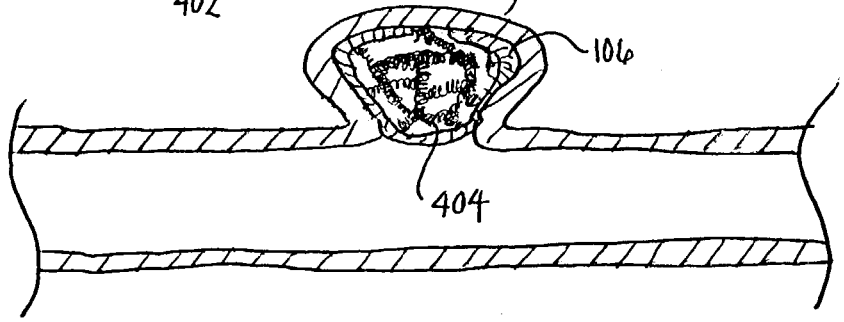

FIG. 4E shows the aneurysm having vaso-occlusive coils 404 stabilized by detachable arms 106 after catheter 402 has been withdrawn. Note however, that if any vaso-occlusive coils escape from and enter the artery, any of the previously described bifurcated guidewire devices and methods may be used to trap and remove them.

It should be understood that the applications of the bifurcated guidewire and methods of use discussed herein are not limited to use within the vascular system but may include any number of further treatment applications. Other treatment sites may include areas or regions of the body such as organ bodies. Modification of the above-described devices and methods for carrying out the invention, and variations of aspects of the invention that are apparent to those of skill in the art and intended to be within the scope of the claims.

We claim:

1. A method for delivering a stent within a branch of a bifurcated vessel comprising the steps of:
   providing a bifurcated guidewire comprising a proximal end, a distal end, a length therebetween, and at least one bifurcation branching the guidewire into at least two arms, wherein at least one of the arms is controllable and wherein each arm is loaded with a stent and the arms are selectively movable relative to each other;
   advancing the guidewire distally within a bifurcated vessel to provide initial access to the bifurcated vessel without being inserted over another member;
   moving a control member to selectively move the arms relative to each other;

positioning each guidewire arm within a different branch of the bifurcated vessel such that each stent is adjacent to a pre-selected treatment site within each branch;

deploying the stents from the guidewire arms;

removing the guidewire from the vessel.

2. The method of claim 1 further comprising the use of a catheter.

3. The method of claim 1 wherein the step of positioning each guidewire arm within a different branch of the bifurcated vessel is facilitated by radio-opaque techniques.

4. The method of claim 1 wherein the stents are radially self-expanding.

5. The method of claim 1 wherein pressurized saline is used to release the stents from the guidewire arms.

6. The method of claim 1 wherein the number of guidewire arms corresponds to the number of branches of the bifurcated vessel.

7. The method of claim 1 wherein the stents are balloon expandable.

8. The method of claim 7 wherein the guidewire has a lumen and the method further comprises the step of injecting fluid through the lumen to expand the balloon to expand the stents.

9. A method for treating a bifurcated vessel having first and second branches comprising the steps of:

providing a bifurcated guidewire having a bifurcation branching the guidewire into first and second arms;

providing a vessel treatment device on the guidewire distal of the bifurcation of the guidewire;

inserting the bifurcated guidewire into the vasculature so the bifurcation of the guidewire is proximal of a bifurcation of the vessel and the first and second arms of the guidewire extend into the first and second branches, respectively, of the vessel, the guidewire providing initial access to the bifurcated vessel without being inserted over another member to reduce the overall profile of the arms to facilitate vascular access;

selectively operating control member to selectively control the distance between the first and second arms; and deploying the vessel treatment device to treat the vessel.

10. The method of claim 9 wherein the treatment device comprises a first stent.

11. The method of claim 10 wherein the treatment device further comprises a second stent wherein the first stent is positioned on the first arm of the guidewire and the second stent is positioned on the second arm of the guidewire.

12. The method of claim 10 wherein the first stent is self expanding.

13. The method of claim 10 wherein the first stent is balloon expandable.

14. The method of claim 13 wherein the guidewire has a lumen and the method further comprises the step of injecting fluid through the lumen to expand the balloon to expand the stents.

15. The method of claim 9 further comprising the step of inserting the guidewire through a catheter to access the vessel to be treated, the first and second arms emerging from a distal end of the catheter and the bifurcation of the guidewire remaining within the catheter.

* * * * *